United States Patent [19]

Laine et al.

[11] Patent Number: 4,593,563
[45] Date of Patent: Jun. 10, 1986

[54] PROCEDURE FOR DETERMINING VELOCITY OF DISSOLUTION

[75] Inventors: Ensio Laine, Rusko; Jarkko Haapaniemi, Turku, both of Finland

[73] Assignee: Labsystems Oy, Helsinki, Finland

[21] Appl. No.: 647,462

[22] Filed: Sep. 5, 1984

[30] Foreign Application Priority Data

Sep. 6, 1983 [FI] Finland .................................. 833181

[51] Int. Cl.$^4$ .............................................. G01N 5/04
[52] U.S. Cl. .................................. 73/432 R; 177/50; 422/264; 422/266; 73/432 CR
[58] Field of Search .......... 73/432 CR, 432 Z, 432 R, 73/432 PS; 177/50; 422/264 B, 264, 266, 266 H

[56] References Cited

U.S. PATENT DOCUMENTS

| | | | |
|---|---|---|---|
| 1,737,377 | 11/1929 | Kolb | 422/264 X |
| 2,674,889 | 4/1954 | Toof | 73/432 Z |
| 2,879,054 | 3/1959 | Wohler | 177/50 X |
| 3,618,395 | 11/1971 | Melliger | 73/432 Z |
| 3,791,222 | 2/1974 | Goodhort et al. | 73/432 Z |
| 3,802,272 | 4/1974 | Bischoff et al. | 73/432 Z |
| 3,853,481 | 12/1974 | Murray | 422/264 B X |
| 3,990,855 | 11/1976 | Cort et al. | 422/264 B |
| 4,247,298 | 1/1981 | Rippie | 73/432 Z |
| 4,279,860 | 7/1981 | Smolen | 73/432 Z X |
| 4,335,438 | 6/1982 | Smolen | 73/432 Z X |

FOREIGN PATENT DOCUMENTS

| | | | |
|---|---|---|---|
| 2530065 | 3/1977 | Fed. Rep. of Germany | 73/432 Z |
| 3123655 | 1/1983 | Fed. Rep. of Germany | |
| 158227 | 1/1983 | German Democratic Rep. | 73/432 Z |
| 3901 | 11/1983 | PCT Int'l Appl. | 73/432 Z |
| 55853 | 7/1968 | Poland | 73/432 Z |
| 1401663 | 7/1975 | United Kingdom | 73/432 Z |
| 271099 | 8/1970 | U.S.S.R. | 73/432 Z |

OTHER PUBLICATIONS

"Comparison of the Accuracy of Different Types of Dissolution Rate Methods"; Pharmaceutisch Weekblad; 108; pp. 49–53; Dr. G. K. Bolhuis et al.; (1973).

Primary Examiner—Stewart J. Levy
Assistant Examiner—Tom Noland
Attorney, Agent, or Firm—Hopgood, Calimafde, Kalil, Blaustein & Judlowe

[57] ABSTRACT

A method and apparatus for accurately determining the rate of dissolution of solid substances with highly reproducible results is disclosed. The method and apparatus are directed to a system wherein a sample of solid, which may be powdery, is placed in a sample holder which is then immersed in a perfusion chamber. The weight of the sample is measured as a function of time as the sample dissolves. The sample holder has a variable internal volume which adjusts to the amount of sample therein so as to maintain a substantially constant liquid/-solid interface area during dissolution rate measurements.

12 Claims, 2 Drawing Figures

PROCEDURE FOR DETERMINING VELOCITY OF DISSOLUTION

TECHNICAL FIELD

The present invention concerns a procedure by which it is possible to determine velocities of dissolution of solid substances. The invention also concerns an apparatus for carrying out the procedure. The invention is applicable for instance in studying the dissolving of medicines.

BACKGROUND ART

The simplest way to determine the velocity of dissolution is to place the sample, a tablet for instance, in the solvent and to observe the changing of the solution's concentration. The samples are analysed e.g. with a spectrophotometer or by high pressure liquid chromatography. In order that comparable results might be achievable, the experimental conditions such as mixing and sampling must be closely standardized. It is not possible however by this method to achieve results with satisfactory repeatability. Errors are caused e.g. by the fact that the solvent volume decreases as samples are taken and the decrease has to be made up with new solvent; the location of the tablet in the container varies, with the result that the tablet is in different flow conditions at different times; it is difficult to draw the sample at exactly the same point; and small, solid particles of matter tend to be entrained in the sample.

In some methods of determination, a tablet of the substance to be examined is placed in a solvent container in a kind of rotating apparatus. For instance in the standard procedure of U.S. Pharmacopea XIX, the tablet is placed in a basket of a specified kind, this basket being rotated in the solvent under closely standardized conditions. The repeatability of results is poor with this method, too. The results present dispersion for the reason above all that the sampling point cannot be standardized. It is true, though, that the procedure can be improved by automation.

In perfusion methods, the tablet to be examined is placed in a chamber through which solvent is conducted. Following after the chamber, the solvent may be analysed e.g. in a flow-through spectrophotometer, whereby continuous information is gained on the dissolution. The procedure may be applied in the form of an open system (the differential method), in which case all the time new, pure solvent is fed into the chamber, or of a closed system (the integral method) wherein the same solvent is circulated. Even in the perfusion methods, result repeatability is poor.

Some velocity of dissolution determining methods have been comparatively assessed in: Bolhuis, G. K. et al., *Pharmaceutisch Weekblad*, 108, 49–53 (1973).

One of the weak points in procedures known in the art is also their inapplicability in the examination of powdery samples.

SUMMARY OF INVENTION

A velocity of dissolution determining method has now been invented in which the essential feature is that the changing weight of a sample placed in solvent is followed.

The apparatus according to the invention comprises a perfusion chamber and therein a sample holder, suspended from scales.

The sample holder of the invention comprises a downward opening cylindrical container with a plunger pushed downward by spring force, and a net closing the opening of the container. The sample is placed between the plunger and the net in a manner making it fill the whole cross-section area of the cylinder.

The following advantages, among others, are gained by the invention:

the dissolving event can be accurately and rapidly followed, and the results are easy to conduct to further analysis by computer;

no high requirements need be imposed on the purity, homogeneity or exact amount of the solvent;

the surface area of the sample undergoing dissolving is constant during the test;

it is possible to examine tablet as well as powder specimens;

it is also possible in the test to elicit transitions of the substance, if any (e.g. crystallizing in hydrate form);

the apparatus is less expensive than the apparatus in methods employing photometry.

The results obtained by the procedure of the invention have displayed excellent repeatability.

BRIEF DESCRIPTION OF DRAWINGS

The invention is more closely illustrated with the aid of the drawings attached and of examples.

In Examples 1–3 are presented determinations made with a potassium bromide tablet and a sodium chloride tablet and powder.

DETAILED DESCRIPTION

Figure 1:
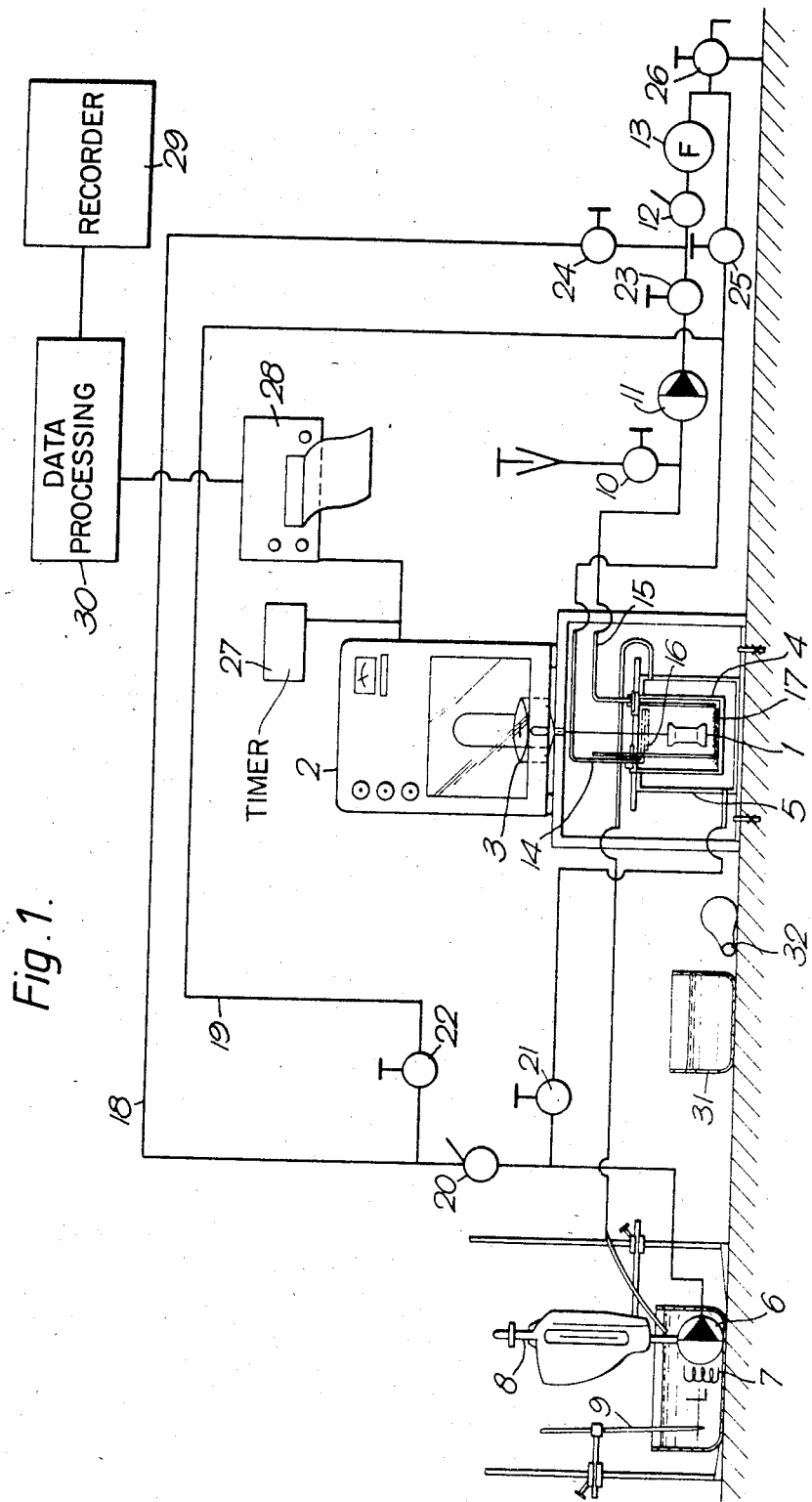
FIG. 1 presents an apparatus employed in the laboratory in carrying out the procedure and FIG. 2, the sample holder used in the apparatus.

In FIG. 1 is seen the sample holder 1, suspended from the pan 3 of the scales 2. The sample holder is immersed in solvent in the perfusion chamber 4. The perfusion chamber has been placed in a water bath 5, where a pump 6 circulates water that has been heated with the aid of a heating resistance 7. The heating resistance is controlled by the thermostat 8, and the water temperature is observed with the thermometer 9. The solvent is introduced in the system through a valve 10, thorugh which the air is also vented. The solvent is moved with the aid of the pump 11 through the control valve 12 and the flow meter 13 by the flexible tube 14 to the top part of the flow chamber. The solvent is removed from the lower part of the flow chamber by the flexible tube 15. In order to standardize the flow conditions and to render the flow laminar, the solvent is admitted into the flow chamber through a plate 16 perforated with closely spaced, small holes. A similar plate 17 has been provided in the lower part of the chamber, the solvent being drained from the chamber through this plate. The apparatus furthermore comprises tubes 18 and 19, and valves 20–26, by the aid of which the solvent circulation can be arranged, e.g. it can be connected with the heating water circuit, or it may be switched to be open. To the apparatus has further been connected, for programming the weights, a timer and for outputting, a printer 28. For the further processing of results there have furthermore been added electronic data processing and recording.

Figure 2:
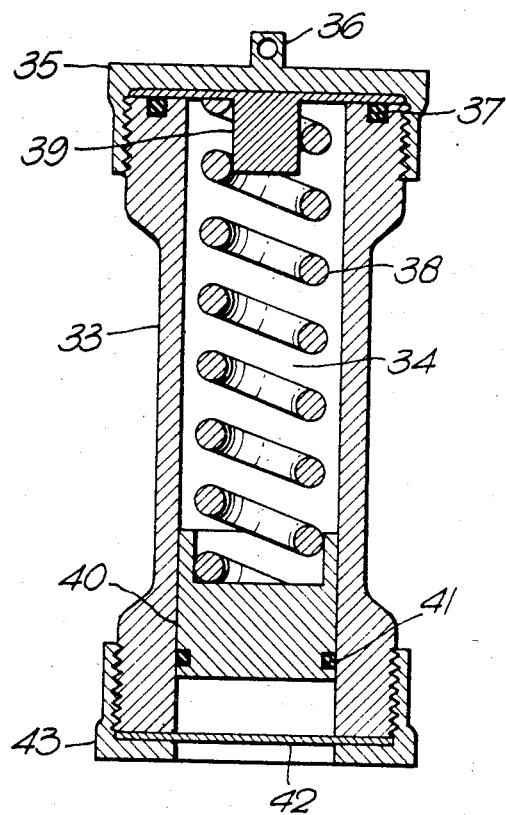

The sample holder in FIG. 2 has a body 33, through which extends a hole 34 having the shape of a circular cylinder. At the top of the holder, the cylinder is closed by a screw cap 35, the cylinder being suspended from the scales by a projection 36 on this cap. The cap is hermetically sealed to the body by means of a gasket ring 37. Within the cylinder is disposed a spring 38, its top end pressing over an intermediate body 39 against the cap of the holder, and the lower end pushing the plunger 40 downwards in the cylinder. The plunger carries a sealing ring 41. The lower end of the cylinder is closed by a net 42, fixed in place by a screwed-on ring 43. It is to be recommended that the holder is made streamlined as to its external shape, for instance oval in shape.

The sample is placed between the plunger and the net. When the volume of the sample decreases by effect of dissolving, the plunger is pushed, by effect of the spring, downward through a corresponding distance. As a result, the added outside volume of holder and sample will be constant, and the influence of buoyancy need not be taken into account.

The sample tablet must have a diameter equalling that of the cylinder in the holder. In the experimental apparatus that was used, the cylinder diameter was 13 mm because tablets of this size have been used as standards in velocity of dissolution studies.

A powdery sample is spread uniformly between the plunger and the net and pressed with the aid of plunger and spring to become a compact layer. The pressure produced in the sample by the spring of the test apparatus, about 0.5 MPa, is in order of magnitude still substantially below the pressure required for pressing into tablet form, and the sample is consequently in powder form still during the test.

The mesh size of the net used on the holder may be varied as required. In the experimental apparatus, mesh sizes between 0.034 and 3.0 mm were used. It is obvious that a small enough mesh is mandatory for powder samples. Changing the mesh size of the net also entails a change of the contact surface between sample and solvent. This surface area was calculated from optic micrographs, and it was between 0.76 and 0.85 $cm^2$ with the nets employed in the experiments. The total area of the sample cylinder was 1.31 $cm^2$. The velocities of dissolution were calculated as referred to the free area of the net. This is not fully justified, however, because the true dissolving surface area between sample and solvent depends, in addition, on the acting cohesive and adhesive forces and on the thickness of the wire and that of the diffusion layer. But the surface area is constant in this procedure throughout the test, as evidenced by the fact that the quantity of substance dissolved per unit time is constant.

The air that has been absorbed on the holder has to be removed prior to immersion in the flow chamber. This is done in the apparatus shown in FIG. 1 by immersing the holder (with the sample in place) in a solvent container 31 and rinsing it powerfully using a rubber pump 32 filled with solvent. When the air has been removed from the holder, the suspension wire is dried and the holder is mounted in its place in the apparatus. The flow is allowed to continue for some time before the measurements are started. The flow causes some variation in the results of weighing, and it is therefore advisable to use for result of measurement e.g. the mean of five consecutive measurements. The measurement is best performed by weighing the sample automatically and conveying the results of weighing directly to a computer to be processed.

The measurement is best carried out using closed circulation so that the solvent flows in the chamber downward from above, but other flow arrangements are also possible. Open circulation may be used particularly in cases in which the solubility of the substance is very low.

The sample holder of the invention is also well applicable in velocity of dissolution determining methods of other types.

EXAMPLE 1

Potassium Bromide Tablet

With an apparatus as depicted in the drawings, the velocity of dissolution of a 500-mg potassium bromide tablet (compressed under 200 MPa) in distilled water at 20.5° C. was determined. The net used on the sample holder had free area 0.809 $cm^2$, the water volume was 1500 ml and the water flow rate, 100 ml/min. The weight of the tablet was measured every 10 seconds, during one minute. The test was performed five times and from the results was calculated by the method of least squares the velocity of dissolution, for which was found the value $2.156 \pm 0.30$ mmol/(min * $cm^2$) (coefficient of correlation: 0.995).

EXAMPLE 2

Sodium Chloride Powder

Similarly as in Example 1, using a net with free area 0.809 $cm^2$, the velocity of dissolution of a sodium chloride powder was measured. The measuring time was 5 min., and the test was performed three times. The velocity of dissolution was found to be $2.990 \pm 0.020$ mmol/(min * $cm^2$) (coefficient of correlation: 0.997).

EXAMPLE 3

Sodium Chloride Tablet

Similarly as in Example 2 was measured the velocity of dissolution of a tablet pressed of sodium chloride powder (pressed under 200 MPa), and this was found to be $1.472 \pm 0.012$ mmol/(min * $cm^2$) (coefficient of corrleation: 0.997).

We claim:

1. A method for determining the rate of dissolution of a solid in a liquid solvent comprising the steps of:
   disposing a sample of said solid in a sample holder with an opening for defining a liquid-solid interface so that a boundary surface of said sample is arranged for contact with said solvent,
   mounting said sample holder on means for weighing said sample as a function of time,
   immersing said sample holder in a dissolution chamber filled with said solvent so that said boundary surface of said sample is in contact with said solvent,
   measuring the weight of said sample as a function of time as said sample dissolves in said liquid, and
   varying the internal volume of said sample holder as said sample dissolves so that the area of said boundary surface in contact with said solvent remains substantially constant throughout said step of measuring the weight of said sample as a function of time.

2. The method according to claim 1, further comprising the step of circulating said solvent about said sample holder with pump means while said sample holder is immersed in said solvent.

3. The method according to claim 2, wherein said step of circulating said solvent comprises introducing said solvent into said dissolution chamber through first means for maintaining laminar flow in said chamber and withdrawing said solvent from said chamber through second means for maintaining laminar flow in said dissolution chamber.

4. The method according to claim 3 wherein said first and second means for maintaining laminar flow in said dissolution chamber comprise a pair of perforated plates.

5. An apparatus for determining the rate of dissolution comprising:

a dissolution chamber for containing a liquid solvent provided with means for introducing solvent at the upper portion thereof and means for withdrawing solvent from the lower portion thereof;

a sample holder defining a cavity for receiving samples of solid, means for supporting said sample holder within said dissolution chamber, said support means and said sample holder being constructed and arranged so that said cavity of said sample holder has a downwardly directed liquid/solid interface-defining opening when positioned in said dissolution chamber whereby sample disposed in said sample holder is arranged for contact with solvent in said dissolution chamber at a boundary surface of said sample at said opening, and means for continuously weighing said sample container, said sample container further including means responsive to the amount of solid in said container for varying the volume of said cavity in accordance with the amount of said sample therein, whereby the area of said boundary surface of said sample in contact with liquid in said dissolution chamber remains substantially constant during dissolution rate measurements.

6. The apparatus according to claim 5, further comprising first means for maintaining laminar flow positioned at the upper portion of said dissolution chamber and second means for maintaining laminar flow positioned at the lower portion of said dissolution chamber.

7. The apparatus according to claim 6, wherein said first and second means for maintaining laminar flow comprise a pair of perforated plates.

8. The apparatus according to claim 5, wherein said sample holder comprises an elongated body with a bore extending longitudinally therethrough over its entire length defining at its lower end said downwardly directed opening, a cap detachably secured to said body for sealing the upper end of said bore and wherein said means for varying the volume of said cavity comprise a plunger journalled in said bore biased for sliding translation toward said downwardly directed opening.

9. The apparatus according to claim 8, further comprising first gasket means for sealing said cap against said body and second gasket means for sealing said plunger against the sidewalls of said bore.

10. The apparatus according to claim 9, wherein said bore is cylindrical.

11. The apparatus according to claim 8, further comprising a meshed member secured to said elongated body adjacent said downwardly directed opening for retaining solid to be analyzed between said plunger and said meshed member.

12. The apparatus according to claim 11, wherein said meshed member is detachably secured to said elongated body.

* * * * *